United States Patent
Hayashizaki

(10) Patent No.: US 6,333,156 B1
(45) Date of Patent: *Dec. 25, 2001

(54) METHOD FOR DETECTING OLIGONUCLEOTIDES AND DETERMINING BASE SEQUENCE OF NUCLEIC ACIDS

(75) Inventor: Yoshihide Hayashizaki, 22-1-201, Inarimae, Tsukuba-shi, Ibaraki-ken (JP)

(73) Assignees: Yoshihide Hayashizaki, Ibaraki; The Institute of Physical and Chemical Research, Saitama, both of (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/354,565

(22) Filed: Jul. 16, 1999

(30) Foreign Application Priority Data

Jul. 17, 1998 (JP) .................................................. 10-203619

(51) Int. Cl.[7] .............................. C12Q 1/68; C12P 19/34; G01N 33/566; C07H 21/02; C07H 21/04
(52) U.S. Cl. .......................... 435/6; 435/91.1; 435/91.52; 436/501; 436/800; 536/23.1; 536/24.32
(58) Field of Search .......................... 435/6, 91.1, 91.52; 436/501, 800; 536/23.1, 24.32

(56) References Cited

U.S. PATENT DOCUMENTS 5,618,701 * 4/1997 Landergren .......................... 435/91.1
5,763,175   6/1998 Brenner ..................................... 435/6

FOREIGN PATENT DOCUMENTS 0284660  10/1988 (EP).
0731173   9/1996 (EP).

OTHER PUBLICATIONS

Connell et al., "Automated DNA sequence analysis", BioTechniques, vol. 5(4), pp. 342–348, 1987.*
Maxam et al., "A new method for sequencing DNA", Proceedings of the National Academy of Sciences (USA), vol. 74 (2), pp. 560–564, Feb. 1977.*
James M. Prober, et al., "A System for Rapid DNA Sequencing with Fluorescent Chain–Terminating Dideoxynucleotides", Science, vol. 238, Oct. 16, 1987, pp. 336–341.

* cited by examiner

*Primary Examiner*—Jeffrey Fredman
*Assistant Examiner*—Arun Kr. Chakrabarti
(74) *Attorney, Agent, or Firm*—Wenderoth, Lind & Ponack, L.L.P.

(57) ABSTRACT

Disclosed are a method which can simultaneously analyze a plurality of analytes and can realize the determination of the base sequence of a large quantity of gene information in a short time, and an apparatus for the method. The method comprises the steps of: preparing four samples, for each of a plurality of nucleic acid analytes, containing analyte nucleic acid-derived oligonucleotide fragments with the end bases having been base-specifically fragmented; labeling the oligonucleotide fragments with a different label for each of the analyte nucleic acids; and subjecting the four samples to an analytical method which can distinguish oligonucleotide fragments based on a difference in length of one base, thereby determining the base sequence of the target nucleic acids.

24 Claims, 4 Drawing Sheets

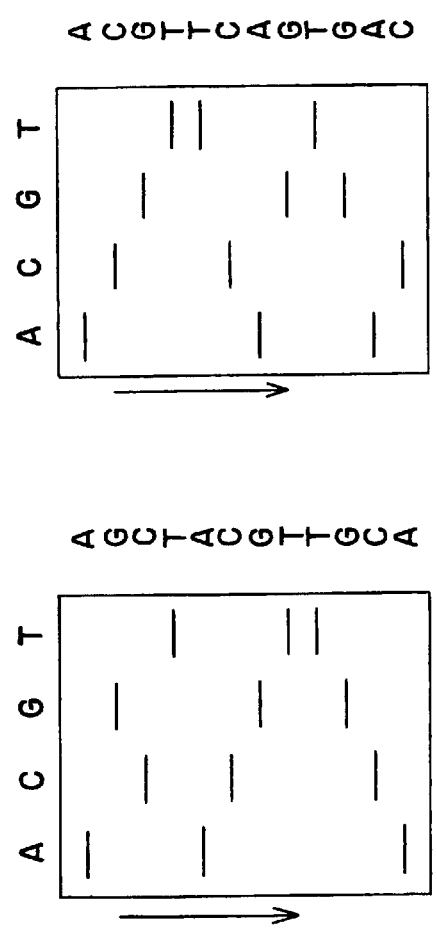
F I G. 1

METHOD FOR DETECTING OLIGONUCLEOTIDES AND DETERMINING BASE SEQUENCE OF NUCLEIC ACIDS

BACKGROUND OF THE INVENTION

1. Field of the Invention

The present invention relates to a method for determining the base sequence of nucleic acids, and an apparatus for said methods.

2. Background Art

Determining and specifying the base sequence of nucleic acids, particularly DNAs (deoxyribonucleic acids) and RNAs (ribonucleic acids), are important for elucidating genetic information and biological information of animals (human beings), plants, bacteria, viruses and the like.

Representative conventional methods for determining the base sequence of nucleic acids include a method, called "Sanger method" or "chain termination method," developed by F. Sanger and A. R. Coulson, and a method, called "Maxam-Gilbert method" or "chemical cleavage method," developed by A. Maxam and W. Gilbert.

The Sanger method will be briefly explained. A DNA fragment to be sequenced is first introduced into a single stranded DNA phage (for example, M13phage) and cloned. This recombinant DNA is used as a template to anneal a primer DNA, and a complementary oligonucleotide fragment is synthesized using a DNA polymerase. In this case, four deoxynucleotide phosphates as substrates and dideoxynucleotide phosphate as a reaction terminator are added to four separate reaction systems. Upon incorporation of dideoxynucleotide into oligonucleotide being synthesized, the synthesis of the oligonucleotide is terminated. As a result, various lengths of DNA fragments ending with dideoxynucleotide are synthesized. The DNA fragments are electrophoresed on a polyacrylamide gel to detect the fragments based on the label possessed by the DNA fragments, thereby determining the base sequence of the target DNA.

Next, the Maxam-Gilbert sequencing method will be briefly explained. The end of DNA to be sequenced is first labeled, and specific one or two bases are chemically cleaved. In this case, reaction conditions are set so that only several sites are nicked in any DNA. Treatment with piperidine permits DNA to be cut at the cleaved base site to provide various lengths of labeled fragments and unlabeled fragments. Only labeled fragments are involved in the sequencing. The larger the distance of the cleaved base from the labeled one end, the larger the size of the fragment. Electrophoresis permits the distance of the labeled one end to the cleaved base to vary according to the electrophoretic mobility. In this method, it is common practice to carry out the above chemical reaction so that four chemical reactions are carried out respectively to cleave only G, only G and A, only T and C, and only C.

On the other hand, in recent years, an attempt has been made to analyze genomes in a large number of organism species including human beings. In this attempt, there is a strong demand for processing of a large quantity of gene information in a short time. This has led to several proposals on the modification of conventional methods to process a large amount of gene information in a short time. For example, multi-capillary electrophoresis using a plurality of capillary columns has been proposed and put to practical use for processing of a large quantity of gene information in a short time. This method is advantageous in that a plurality of analytes can be analyzed. In this method, however, when one analyte is analyzed, four capillaries should be provided respectively for the bases. In order to simultaneously analyze a plurality of analytes, the number of capillaries should be further increased for each analyte. On the other hand, analysis of one analyte has been carried out using one capillary with a different label being used for each base. In this method, however, for simultaneous analysis of a plurality of analytes, the number of capillaries should be simply increased. Most of multi-capillary electrophoresing devices are constructed so that a plurality of capillaries are scanned by a laser beam or the like to read labels. Therefore, increasing the number of capillaries results in increased width to be scanned, leading to a fear of the detection accuracy being lowered.

Therefore, the development of a method for simultaneously analyzing a plurality of analytes in an efficient and accurate manner has still been desired in the art.

So far as the present inventor knows, there is no report that, in simultaneously analyzing a plurality of analytes by sequencing based on the Sanger method or the Maxam-Gilbert method, oligonucleotide fragments are simultaneously analyzed with a different label being used for each analyte.

SUMMARY OF THE INVENTION

The present inventor has now found that, in simultaneously analyzing a plurality of analytes according to the Sanger method or the Maxam-Gilbert method, use of a different label for each analyte and labeling of oligonucleotide fragments, which have been specifically fragmented with respect to four end bases and are derived from an identical analyte, with an identical labeling material can realize simultaneous analysis of a plurality of analytes with very high efficiency.

Accordingly, it is an object of the present invention to provide a method which can simultaneously analyze a plurality of analytes and can determine the base sequence of a large amount of gene information in a short time, and an apparatus for the method.

According to one aspect of the present invention, there is provided a method for determining the base sequence of target nucleic acids contained in a plurality of analytes, said method comprising the steps of:

(a) providing a plurality of nucleic acid analytes containing respective target nucleic acids;

(b) preparing four samples, for each of the plurality of the nucleic acid analytes, containing various lengths of labeled oligonucleotide fragments respectively having sequences identical to or complementary to a part of the target nucleic acid, the oligonucleotide fragments at their end bases having been base-specifically fragmented, the oligonucleotide fragments having been labeled with a different label for each of the nucleic acid analytes;

(c) subjecting the four samples for each of the nucleic acid analytes to a separation method which can simultaneously distinguish oligonucleotide fragments for each type of end bases, independently of the nucleic acid analytes from which the oligonucleotide fragments have been derived, based on a difference in length of one base; and (d) detecting the separated oligonucleotide fragments based on the labels and analyzing the length of the oligonucleotide fragments one base by one base to determine the base sequence of the target nucleic acids.

The method for determining the base sequence of a target nucleic acid in a plurarity of analytes according to the present invention is based on the fact that the information on the length of oligonucleotide is obtained one base by one base. Thus, according to a second aspect of the present invention, there is provided a method for simultaneously analyzing the length of oligonucleotides, necessary for the determination of the final base sequence, one base by one base for a plurality of sample sets, said method comprising the steps of:

providing a plurality of sample sets each consisting of four samples containing various lengths of labeled oligonucleotide fragments, the oligonucleotide fragments at their end bases having been base-specifically fragmented, the oligonucleotide fragments having been labeled with a different label for each of the sample set;

subjecting the four samples for each of the sample sets to a separation method which can simultaneously distinguish oligonucleotide fragments for each type of end bases, independently of the sample sets, based on a difference in length of one base; and detecting the separated oligonucleotide fragments based on the labels and analyzing the length of the oligonucleotide fragments one base by one base.

According to a third aspect of the present invention, there is provided an apparatus for simultaneously analyzing the length of oligonucleotides one base by one base for a plurality of sample sets, said apparatus comprising:

test sample holding means for holding a test sample obtained by separating labeled oligonucleotide fragments based on a difference in the length of one base;

label excitation means for exciting a label when the label requires to be excited by external energy for emission of a signal; and detection means for detecting a signal from the label and analyzing the length of oligonucleotide fragments one base by one base, said test sample having been obtained by providing a plurality of sample sets each consisting of four samples containing various lengths of labeled oligonucleotide fragments, the oligonucleotide fragments at their end bases having been base-specifically fragmented, the oligonucleotide fragments having been labeled with a different label for each of the sample sets, and subjecting the four samples for each of the sample sets to a separation method which can simultaneously distinguish oligonucleotide fragments for each type of end bases, independently of the sample sets, based on a difference in length of one base.

BRIEF DESCRIPTION OF THE DRAWINGS

FIG. 1 is a diagram showing an electrophoresis pattern for two analytes a and b, wherein FIG. 1(A) and FIG. 1(B) are electrophoresis patterns respectively for analytes a and b and FIG. 1(C) is a pattern obtained by simultaneous electrophoresis of two analytes a and b;

DESCRIPTION OF THE PREFERRED EMBODIMENTS

Figure 2:
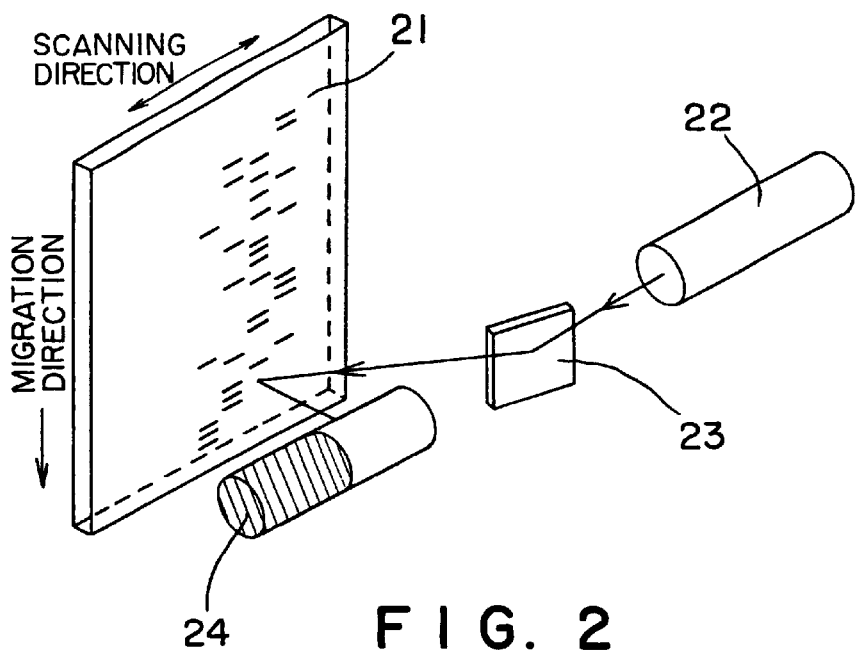
FIG. 2 is an explanatory view of the fundamental structure of an analyzer according to the present invention.

Method according to first aspect of present invention

In the method according to the first aspect of the present invention, the base sequence of target nucleic acids contained in a plurality of samples containing the respective target nucleic acids is determined.

Step (a)

Step (a) as the first step is to provide a plurality of nucleic acid analytes containing respective target nucleic acids.

The length of target nucleic acids, the base sequence of which can be determined by the method according to the present invention, is generally about 1200 bP when a gel having a length of about 200 mm, a width of 360 mm, and a thickness of 0.2 mm is used. In the method according to the present invention, however, the length of target nucleic acid to be determined varies depending upon the length of gel used, constituents, and conditions for electrophoresis and hence is not limited to the above length. This could be easily understood by a person having ordinary skill in the art. When specifying the base sequence of a gene having a length exceeding the above length is contemplated, a method may be used which comprises: bringing the gene to fragments, with approximately the above length, having overlapped sequences; determining the base sequence of the fragments; and determining the whole sequence of the gene while specifying the overlapping sequences. Accordingly, in the present invention, the target nucleic acids contained in the plurality of analytes provided in this first step will generally have partial sequences of a nucleic acid having a certain sequence and are overlapped with each other or one another in a certain sequence range.

In the method according to the present invention, however, it is a matter of course that these target nucleic acids may be such that the target nucleic acids are derived from utterly different genes and, unlike the above case, there is no overlapped sequence range in the target nucleic acids.

Step (b)

Next, for each of the nucleic acid analytes, four samples are prepared which contain various lengths of labeled oligonucleotide fragments respectively having sequences identical to or complementary to a part of the target nucleic acid, the oligonucleotide fragments at their end bases having been base-specifically fragmented. According to the present invention, the oligonucleotide fragments should be labeled with a different label for each of the nucleic acid analytes.

It is well known that, in the case of DNA, nucleic acids consist of four bases of A (adenine), T (thymine), G (guanine), and C (cytosine). Consequently, end base information of at least four suffices for learning the base sequence of a certain nucleic acid from a large number of fragments thereof. Therefore, in the present invention "four samples wherein the oligonucleotide fragments at their end bases have been base-specifically fragmented" refers to four samples of oligonucleotide fragments respectively ending with four bases which provide information on the base sequence of the nucleic acid. The four samples, for example, may be those wherein the end of the oligonucleotide in one sample consists of A only, the end of the oligonucleotide in another sample consists of T only, the end of the oligonucleotide in still another sample consists of G only, and the end of the oligonucleotide in a further sample consists of C only.

Further, the base sequence may be learned from four samples wherein the end of the oligonucleotide consists of G only for one sample, G and A only for another sample, T and C only for still another sample, and C only for a further sample. Therefore, such four samples are also utilizable in the present invention.

This step may be substantially the same as the step of preparation performed in the Sanger method or the Maxam-Gilbert method. However, the label should be changed for each of the nucleic acid analytes, and the four samples derived from an identical nucleic acid analyte should be labeled with an identical labeling material.

The type of the label is not particularly limited so far as it, upon excitation by external energy or without such energy, can emit a recognizable signal. The label may be introduced by any method which has been properly selected according to the type of the label. It would be evident that when this step is carried out according to the Sanger method, the label should not inhibit the incorporation of the oligonucleotide and the elongation by polymerase, while when this step is carried out according to the Maxam-Gilbert method, the label should be introduced into one end of the target nucleic acid.

Labels usable in the present invention include radioactive elements, fluorescent labels, and labeling by enzymatic reaction. According to the present invention, a plurality of analytes are simultaneously analyzed. Therefore, use of fluorescent labeling reagents is preferred, because a large number of labels having similar properties are known in the art. Specific examples of fluorescent labeling reagents, which may be preferably used in the present invention, include those indicated in the following table.

| Name | Excitation wavelength, nm | Wavelength of fluorescence, nm |
| --- | --- | --- |
| Bodipy-fluorescein | 503 | 513 |
| Rhodamine | 499 | 521 |
| 7-Nitrobenz-2-oxa-1,3-diazole | 465 | 535 |
| Rhodamine 6 G | 525 | 555 |
| Cy3 | 552 | 570 |
| Tetra methyl rhodamine | 555 | 580 |
| X-rhodamine | 580 | 605 |
| Cy5 | 643 | 667 |

As described above, the introduction of the label into the oligonucleotide (fragment) according to the present invention may be carried out by any proper method. For example, a method reported by Prober et. al. may be used (see Prober et. al., (1987) Science 238, 336–341).

Step (c)

In the step (b), four samples are prepared for each of the nucleic acid analytes. In the step (c), these samples are subjected to a separation method which can simultaneously distinguish oligonucleotide fragments for each of the types of end bases, independently of the nucleic acid analytes from which the oligonucleotide fragments are derived, based on a difference in length of one base.

The procedure will be more specifically explained with the reference to FIG. 1. In this embodiment, two nucleic acid analytes, analytes a and b, were provided. For each of the analytes, four samples, wherein the end of the oligonucleotide consists of A only for one sample, C only for another sample, G only for still another sample, and T only for a further sample, are prepared in the above step. These are subjected to a separation method (for example, electrophoresis) which can distinguish oligonucleotide fragments for each of the types of end bases (that is, for each of A, C, G, and T) based on a difference in length of one base. Electrophoresis patterns respectively for the analytes a and b are as shown in FIGS. 1(A) and (B). In the drawing, the direction of electrophoresis is indicated by an arrow. According to the present invention, these samples are simultaneously electrophoresed for each of the types of end bases independently of analytes a and b. The resultant electrophoresis pattern is as shown in FIG. 1(C). According to the present invention, the oligonucleotide samples are labeled with an identical label when they are derived from an identical analyte, that is, analyte a or analyte b. The label for the oligonucleotide samples derived from analyte a is different from the label for the oligonucleotide samples derived from analyte b. For example, in analytes a and b, all the ends of the shortest migration distance, that is, all the ends of the longest oligonucleotides, are A. These oligonucleotide fragments are overlapped on lane A. Since, however, analytes a and b are labeled with different labels, the difference in label permits distinguishment of analytes a and b from each other. Likewise, in the oligonucleotide fragments in analytes a and b, overlapping often occurs due to the same fragment length (in the drawing, bands appended with "a, b"). These fragments can be distinguished from each other by virtue of the difference in label.

According to the present invention, even though the number of analytes are increased, all the analytes can be distinguished from one another on four lanes by using a different label for each of the analytes. In the conventional method wherein a different label is used for each of the end bases, increasing the number of analytes has required increasing the number of lanes. By contrast, the present invention is very advantageous in that a large number of analytes can be distinguished on four lanes. This advantage is particularly significant in multi-capillary electrophoresis using a plurality of capillary columns. Specifically, when the present invention is applied to this method, basically, use of four capillaries suffices for the electrophoresis. Further, when the label is read by a laser beam, the width to be scanned is the total width of the four capillaries. This is very advantageous from the viewpoint of optical reading accuracy.

The "separation method which can distinguish oligonucleotide fragments based on a difference in length of one base" performed in this step is not particularly limited. However, currently widely used electrophoresis is preferred. Particularly preferred is gel electrophoresis using a gel as a support. Polyacrylamide gel/sodium dodecylsulfate electrophoresis is most preferred. The preparation of gel, voltage applied, temperature conditions and the like may be properly determined. Further, it is apparent that the preparation of gel and various conditions could be determined by a person having ordinary skill in the art without necessity of unreasonable experiments.

Step (d)

In step (d), the separated oligonucleotide fragments are detected based on the label, and the length of the oligonucleotide fragments is analyzed one base by one base to determine the base sequence of the target nucleic acid. After the length of the oligonucleotide fragments is separated one base by one base in the above step, information on the length is obtained through the label. As described above, the label emits a signal upon exposure to external energy or without such energy. Therefore, the signal output according to the properties of the label can be recognized to obtain information on the length of the oligonucleotide fragments. More specifically, for example, when the label is a fluorescent labeling reagent, the label is excited by application of light containing excitation wavelength, followed by detection of the resultant fluorescence.

As described above, when electrophoresis is used as the separation method which can distinguish oligonucleotide fragments based on a difference in length of one base, the difference in length of oligonucleotide fragments appears as the difference in mobility. According to the present invention, the migration distance of the oligonucleotide fragments can be learned through the label, and the length of the oligonucleotide fragments can be learned one base by one base. The end bases are placed in the order of the length of the oligonucleotide fragments to obtain the base sequence of the target nucleic acid. According to the present invention, a plurality of analytes are simultaneously analyzed. As a result, information on the base sequence of a plurality of target nucleic acids can be very efficiently obtained. It would be apparent to a person having ordinary skill in the art that, when the plurality of target nucleic acids are partial sequences of a certain gene and have overlapped sequence range, the whole sequence of the certain gene can be determined by determining the base sequence of the target nucleic acids and determining the whole sequence while specifying the overlapping sequences.

Method according to second aspect of present invention

The method according to the first aspect of the present invention aims to determine the base sequence of certain nucleic acids. The method for determining the base sequence of target nucleic acids according to the first aspect of the present invention is based on the fact that information on the length of oligonucleotides is obtained one base by one base. Therefore, a method, which can obtain information on the length of oligonucleotides one base by one base, per se also is of technical significance. In the present invention, this method will be hereinafter referred to as the second aspect of the present invention. Thus, according to the second aspect of the present invention, there is provided a method for simultaneously analyzing the length of oligonucleotides necessary for the determination of the final base sequence one base by one base for a plurality of sample sets.

This method according to the second aspect of the present invention is quite the same as that according to the first aspect of the present invention, except that the step of determining the base sequence is excluded. Specifically, a plurality of sample sets each consisting of four samples containing various lengths of labeled oligonucleotide fragments with the oligonucleotide fragments at their end bases having been base-specifically fragmented are provided. This step is substantially identical to steps (a) and (b) in the first aspect of the present invention. The introduction of a label into the oligonucleotide fragments may also be carried out in the same manner as that in the step (b). The four samples for each of the sample sets are then subjected to a separation method which can simultaneously distinguish oligonucleotide fragments for each type of end bases, independently of the sample sets, based on a difference in length of one base. This step may be substantially identical to step (c) in the first aspect of the present invention. Further, the detection of the separated oligonucleotide fragments based on the labels may also be carried in the same manner as in the step (d) according to the first aspect of the present invention.

Apparatus

According to the third aspect of the present invention, there is provided an apparatus for simultaneously analyzing the length of oligonucleotides one base by one base for a plurality of sample sets. This apparatus basically comprises: test sample holding means for holding a test sample obtained by separating labeled oligonucleotide fragments based on a difference in the length of one base; label excitation means for exciting a label when the label requires to be excited by external energy for emission of a signal; and detection means for detecting a signal from the label and analyzing the length of oligonucleotide fragments one base by one base. In this case, the test sample has been obtained by providing a plurality of sample sets each consisting of four samples containing various lengths of labeled oligonucleotide fragments, the oligonucleotide fragments at their end bases having been base-specifically fragmented, the oligonucleotide fragments having been labeled with a different label for each of the sample sets, and subjecting the four samples for each of the sample sets to a separation method which can simultaneously distinguish oligonucleotide fragments for each type of end bases, independently of the sample sets, based on a difference in length of one base.

According to a preferred embodiment of the present invention, when the label is a fluorescent labeling reagent, the label excitation means for exciting labels comprises: light irradiation means; and scanning means for scanning light emitted from the light irradiation means on the test sample. The detection means comprises: means for separating different fluorescences emitted from the different labels for respective sample sets; and means for detecting separated fluorescences.

The fundamental construction of the analyzer according to the present invention will be explained with reference to FIG. 2.

In the drawing, the test sample is an electrophoretic gel plate 21. In the electrophoretic gel plate 21 obtained according to the first or second aspect of the present invention, labeled oligonucleotide fragments derived from a plurality of analytes are electrophoresed in a direction indicated by an arrow in the drawing. This gel plate 21 is irradiated with light containing excitation lights for all the labels from an light irradiation apparatus 22 (for example, a laser beam irradiation device). A mirror 23 as the scanning means is moved to perform scanning in a direction indicated by an arrow in the drawing. When a label is present at a position exposed to the light, the label emits fluorescence. This fluorescence is detected by detection means 24 to obtain positional information of the label. This detection means 24 can function to recognize different fluorescences attributable to the difference in the types of the labels in such a state that they are distinguished from each other. Therefore, even though there are a plurality of oligonucleotide fragments on the same position, the samples, from which the oligonucleotides are derived, can be detected according to the difference in label. Further, according to another embodiment of the present invention, the light irradiation device 22 applies different light for each of the labels. In this case, there is no need for the detection means 24 to have such a function that can recognize different fluorescences attributable to the difference in the types of labels in the state of distinguishment of the different fluorescences from each other. This function, however, is preferred from the viewpoint of more accurate detection.

In FIG. 2, when the electrophoresis is carried out using a multi-capillary, four capillaries filled with a gel may be used as the test sample instead of the electrophoretic gel plate 21.

Figure 3:
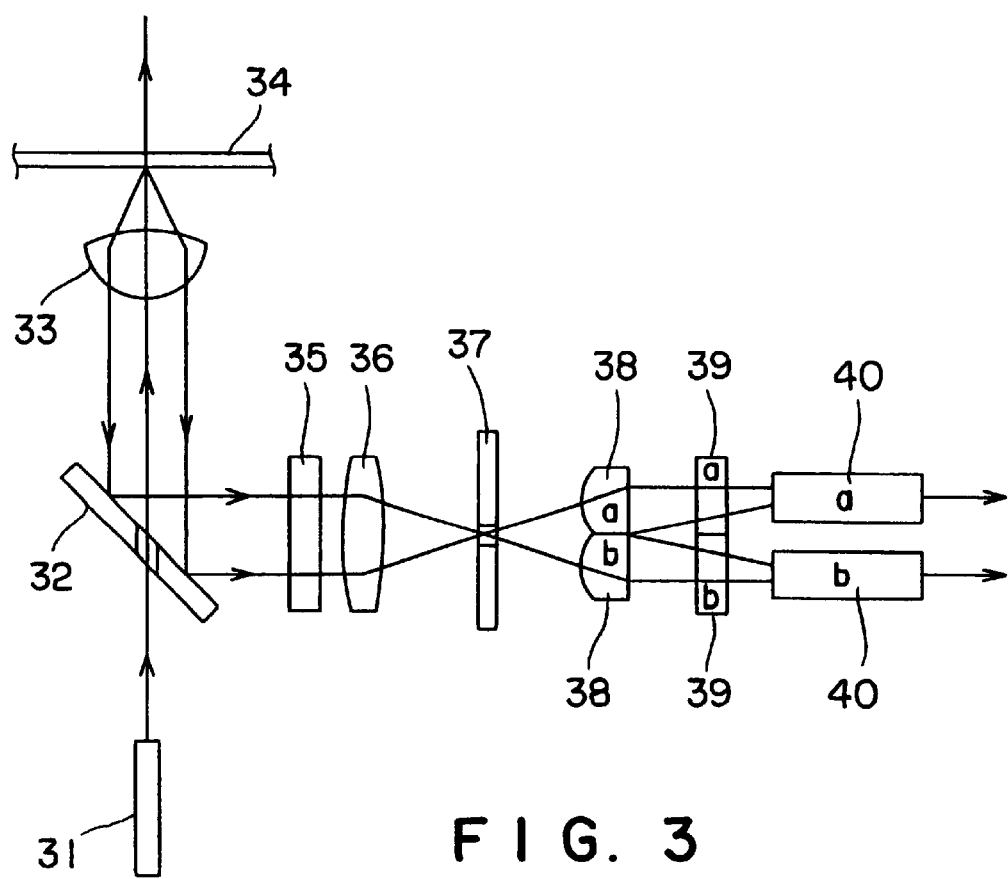
FIG. 3 is a diagram showing an optical system according to one embodiment of the analyzer according to the present invention.

The label excitation means and the detection means in the analyzer according to the present invention will be explained in more detail with reference to FIG. 3. The system shown in this drawing is used in the case where two analytes have been labeled respectively with two different labels. In FIG. 3, a laser beam applied from a laser irradiation device 31 as an excitation source enters a tunnel mirror 32. The tunnel mirror 32 has in its center a hole, and the excitation light beam is passed through the hole. The laser beam passed through the tunnel mirror 32 enters a condensing lens 33 and applied to the electrophoretic gel plate 34. The condensing lens 33 performs both the application of the excitation light beam and the receipt of fluorescence in the single lens, and constitutes a reflection optical system. The fluorescence condensed by the condensing lens 33 is reflected from the specular surface of the tunnel mirror 32.

An optical filter 35 cuts off the excitation light components from the reflected light and permits fluorescence to be passed therethrough. An edge filter for removing the excitation light and a color glass may be utilized as the optical filter 35. A pinhole slit 37 functions to limit the visual field for the detection and to prevent the entrance of stray light of the adjacent base. A stopping lens 36 serves to form an image of the fluorescence, passed through the optical filter 35, at the position of the pinhole slit 37. Image formation of the fluorescence creation point of the fluorescence-labeled base within the gel at the position of the pinhole slit 37 constitutes a confocal optical system.

A two-divided lens panel 38 is disposed for dividing the fluorescent image formed at the pinhole slit 37 into two beams. The two-divided lens panel 38 comprises two lenses 38a and 38b which may be prepared by cutting single lenses and laminating them onto each other or prepared as a glass molded product.

Filter panels 39 respectively comprising different spectroscopic filters for fluorescent labeling reagents corresponding to the two analytes are disposed on respective optical paths for the two-divided beams. The filter panels 39 are disposed so that two band-pass filters 39a and 39b having different wavelength characteristics corresponding to fluorescent labeling reagents for the two analytes are located on the respective optical paths. The filter panels 39 permit only fluorescences from the two labels to be passed therethrough. The fluorescences passed through the band-pass filters are detected respectively by two photomultiplier tubes 40a and 40b disposed on the optical paths.

The above construction is for the case where the number of analytes is two. When the number of analytes is increased, for example, to four or six, the four analytes or the six analytes can be distinguished from one another in such a manner that the divided lens panel 38 and the filter panel 39 in FIG. 3 each are divided into 4 parts or six parts and, in addition, the number of photomultiplier tubes 40 is increased to four or six.

Figure 4:
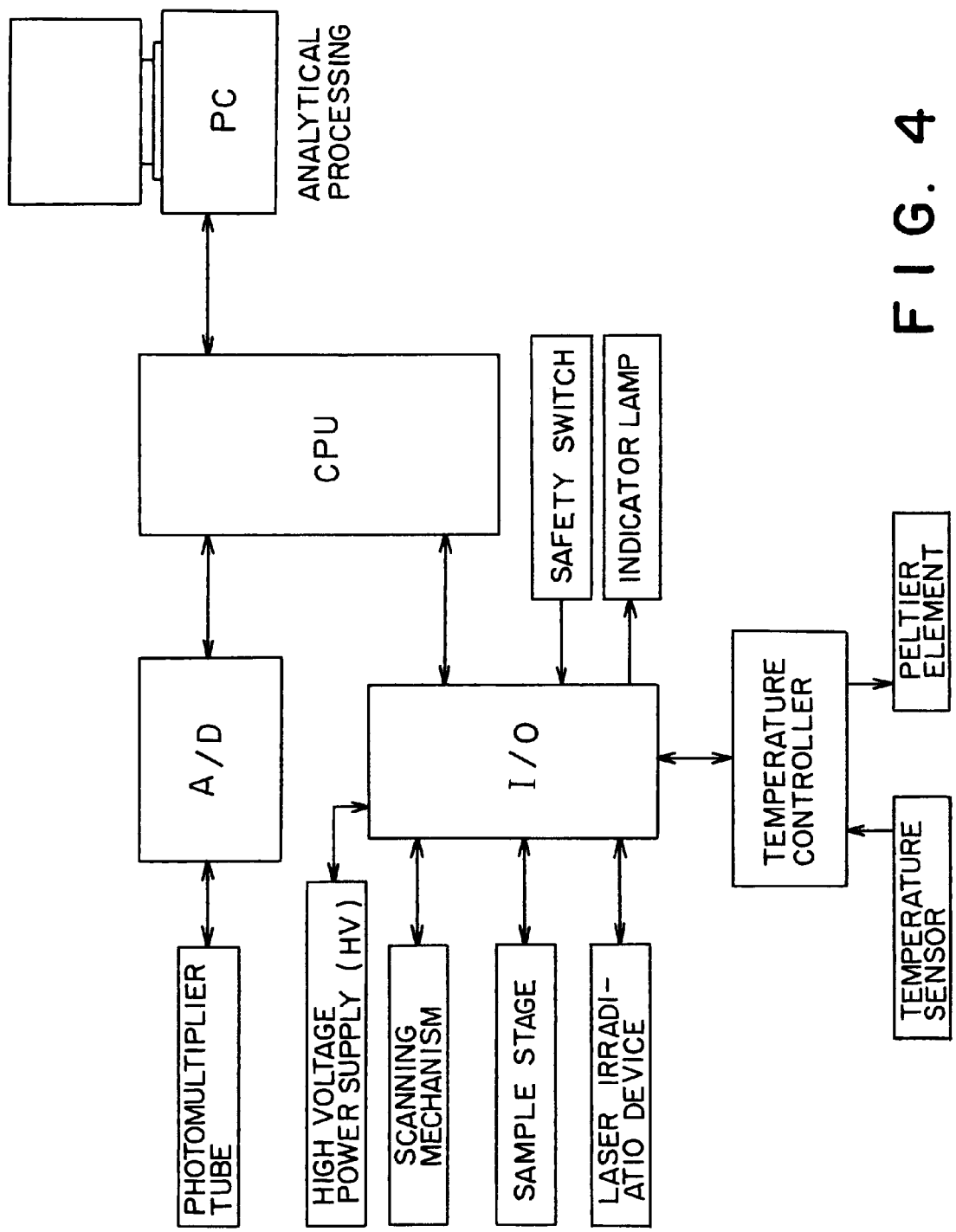
FIG. 4 is a diagram showing a controller provided in the apparatus according to the present invention.

The apparatus according to the present invention further comprises a device for analyzing detection signals from the photomultiplier tubes 40 and a controller. The controller is as shown in FIG. 4. As shown in FIG. 4, the controller comprises: CPU; an A/D converter for converting a detection signal from the photomultiplier tube to a digital signal and incorporating the digital signal into CPU; an I/O interface for outputting a signal to or receiving a signal from each section in response to instruction from CPU; and a temperature controller for controlling the temperature in the electrophoresis. The I/O interface is connected to the temperature controller, a high-pressure power supply for analyte injection and electrophoresis, a sensor and a motor for the scanning mechanism, a sensor and a motor for a sample stage, a power supply for a laser irradiation device, a safety switch for an interlock, an indicator lamp and the like. CPU is connected to an external personal computer (PC) which analyzes information on the length of the detected oligonucleotide fragments to determine the base sequence of the target nucleic acids.

Figure 5:
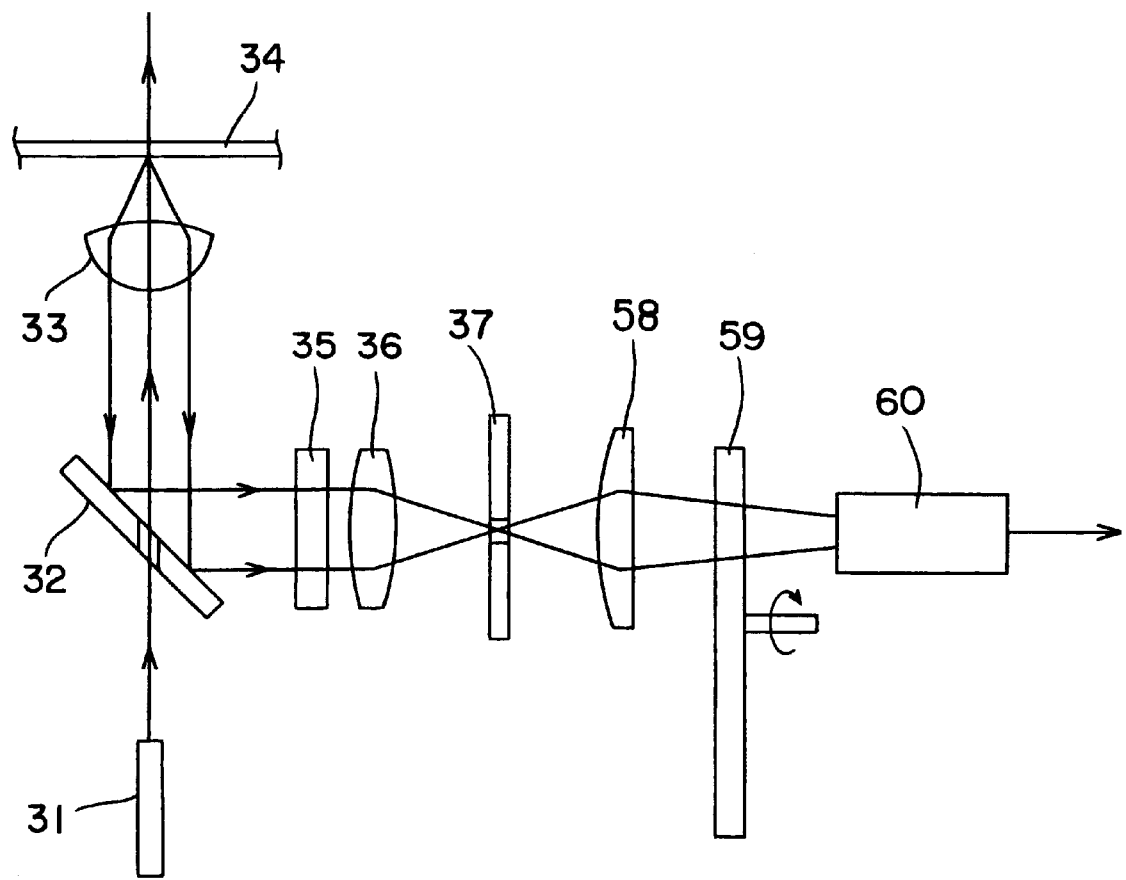
FIG. 5 is a diagram showing an optical system according to another embodiment of the analyzer according to the present invention.

According to another embodiment of the apparatus of the present invention, there is provided an apparatus shown in FIG. 5. In this apparatus, a lens 58 and a band-pass filter array 59 comprising band-pass filters, corresponding respectively to a plurality of fluorescences, set in a circular form are disposed instead of the divided lens panel 38 and the filter panel 39 in the apparatus shown in FIG. 3. One photomultiplier tube 60 is installed behind the band-pass filter array 59. In FIGS. 3 and 5, like members have the same reference numerals. This apparatus is advantageous in that rotation of the array 59 while applying light to one point of the gel plate 34 can realize detection and distinguishment of a plurality of fluorescences in a continuous manner by a single photomultiplier.

What is claimed is:

1. A method for determining the base sequence of one or more target nucleic acid(s), said method comprising:

providing a plurality of nucleic acid analyte(s) for each target nucleic acid, each of said nucleic acid analyte(s) corresponding to at least a part of its respective target nucleic acid, said nucleic acid analyte(s) having different nucleotide sequences with respect to each other which are overlapping or non-overlapping, preparing at least four samples for each nucleic acid analyte, said samples each comprising various lengths of oligonucleotide fragments which have sequences identical to or complementary with a part of their respective target nucleic acid, said oligonucleotide fragments of each of said samples being base-specifically fragmented at their end bases such that the base sequence of said oligonucleotide fragments can be determined, labeling each nucleic acid analyte with a different label wherein said samples derived from an identical nucleic acid analyte are identically labeled and said samples derived from a different nucleic acid analyte are differently labeled, combining said samples of two or more nucleic acid analytes in correspondence to their fragmented end bases to obtain at least four combined samples each comprising identically fragmented oligonucleotide fragments from different nucleic acid analytes, separating said combined samples to simultaneously distinguish the oligonucleotide fragments for each kind of end bases based on a difference in length of one base, detecting the separated oligonucleotide fragments based on their respective labels and analyzing the length of the oligonucleotide fragments one base at a time to determine the base sequence of said target nucleic acid(s).

2. The method according to claim 1, wherein sets of four samples are prepared and the four samples consist of (a) a sample with an end base consisting of A only, (b) a sample with an end base consisting of C only, (c) a sample with an end base consisting of G only, and (d) a sample with an end base consisting of T only.

3. The method according to claim 1, wherein sets of four samples are prepared and the four samples consist of (a) a sample with an end base consisting of G only, (b) a sample with an end base consisting of G and A only, (c) a sample with an end base consisting of T and C only, and (d) a sample with an end base consisting of C only.

4. The method according to any one of claims 1 to 3, wherein at least one of the labels is a fluorescent labeling reagent.

5. The method according to any one of claims 1 to 3, wherein said combined samples are separated through gel electrophoresis.

6. A method for simultaneously analyzing the length of oligonucleotides one base by one base for a plurality of sample gets said method comprising:

providing a plurality of sample sets, said sample sets each consisting of at least four samples comprising various lengths of oligonucleotide fragments, said oligonucleotide fragments of each of said samples being base-specifically fragmented at their end bases such that the length of said oligonucleotides for the plurality of sample sets can be determined, labeling each sample set with a different label wherein said samples derived from an identical sample set are identically labeled and said samples derived from a different sample set are differently labeled, combining said samples of two or more sample sets in correspondence to their fragmented end bases to obtain at least four combined samples each comprising identically fragmented oligonucleotide fragments from different sample sets, separating said combined samples to simultaneously distinguish the oligonucleotide fragments for each kind of end bases based on a difference in length of one base, detecting the separated oligonucleotide fragments based on their respective labels and analyzing the length of the oligonucleotide fragments one base by one base.

7. The method according to claim 6, wherein sets of four samples are prepared and the four samples consist of (a) a sample with an end base consisting of A only, (b) a sample with an end base consisting of C only, (c) a sample with an end base consisting of G only, and (d) a sample with an end base consisting of T only.

8. The method according to claim 6, wherein sets of four samples are prepared and the four samples consist of (a) a sample with an end base consisting of G only, (b) a sample with an end base consisting of G and A only, (c) a sample with an end base consisting of T and C only, and (d) a sample with an end base consisting of C only.

9. The method according to any one of claims 6 to 8, wherein at least one of the labels is a fluorescent labeling reagent.

10. The method according to any one of claims 6 to 8, wherein said combined samples are separated through gel electrophoresis.

11. The method according to claim 4, wherein said combined samples are separated through gel electrophoresis.

12. The method according to claim 9, wherein said combined samples are separated through gel electrophoresis.

13. A method for determining the base sequence of a plurality of target nucleic acid(s), said method comprising.

providing one or more nucleic acid analyte(s) for each target nucleic acid, each of said nucleic acid analyte(s) corresponding to at least a part of its respective target nucleic acid, said nucleic acid analyte(s) having different nucleotide sequences with respect to each other which are overlapping or non-overlapping, preparing at least four samples for each nucleic acid analyte, said samples each comprising various lengths of oligonucleotide fragments which have sequences identical to or complementary with a part of their respective target nucleic acid, said oligonucleotide fragments of each of said samples being base-specifically fragmented at their end bases such that the base sequence of said oligonucleoride fragments can be determined, labeling each nucleic acid analyte with a different label wherein said samples derived from an identical nucleic acid analyte are identically labeled and said samples derived from a different nucleic acid analyte are differently labeled, combining said samples of two or more nucleic acid analytes in correspondence to their fragmented end bases to obtain at least four combined samples each comprising identically fragmented oligonucleotide fragments from different nucleic acid analytes, separating said combined samples to simultaneously distinguish the oligonucleotide fragments for each kind of end bases based on a difference in length of one base, detecting the separated oligonucleotide fragments based on their respective labels and analyzing the length of the oligonucleotide fragments one base at a time to determine the base sequence of said target nucleic acid(s).

14. The method according to claim 13, wherein sets of four samples are prepared and the four samples consist of (a) a sample with an end base consisting of A only, (b) a sample with an end base consisting of C only, (c) a sample with an end base consisting of G only, and (d) a sample with an end base consisting of T only.

15. The method according to claim 13, wherein sets of four samples are prepared and the four samples consist of (a) a sample with an end base consisting of G only, (b) a sample with an end base consisting of G and A only, (c) a sample with an end base consisting of T and C only, and (d) a sample with an end base consisting of C only.

16. The method according to any one of claims 13 to 15, wherein at least one of the labels is a fluorescent labeling reagent.

17. The method according to any one of claims 13 to 15, wherein said combined samples are separated through gel electrophoresis.

18. The method according to claim 16, wherein said combined samples are separated through gel electrophoresis.

19. The method according to claim 5, wherein the gel electrophoresis is performed on at least four lanes of an electrophoretic slab or at least four gel capillaries.

20. The method according to claim 10, wherein the gel electrophoresis is performed on at least four lanes of an electrophoretic slab or at least four gel capillaries.

21. The method according to claim 11, wherein the gel electrophoresis is performed on at least four lanes of an electrophoretic slab or at least four gel capillaries.

22. The method according to claim 12, wherein the gel electrophoresis is performed on at least four lanes of an electrophoretic slab or at least four gel capillaries.

23. The method according to claim 17, wherein the gel electrophoresis is performed on at least four lanes of an electrophoretic slab or at least four gel capillaries.

24. The method according to claim 18, wherein the gel electrophoresis is performed on at least four lanes of an electrophoretic slab or at least four gel capillaries.

* * * * *